(12) United States Patent
Akahoshi (10) Patent No.: US 8,109,900 B2
(45) Date of Patent: Feb. 7, 2012

(54) COEXTENSIVE TUBING SYSTEM FOR PHACOEMULSIFICATION HANDPIECES

(75) Inventor: Takayuki Akahoshi, Tokyo (JP)

(73) Assignee: Art, Limited, Grand Cayman (KY)

( * ) Notice: Subject to any disclaimer, the term of this patent is extended or adjusted under 35 U.S.C. 154(b) by 829 days.

(21) Appl. No.: 11/680,595

(22) Filed: Feb. 28, 2007

(65) Prior Publication Data

US 2011/0105999 A1    May 5, 2011

Related U.S. Application Data

(63) Continuation-in-part of application No. 11/069,773, filed on Mar. 1, 2005.

(60) Provisional application No. 60/613,645, filed on Sep. 27, 2004, provisional application No. 60/828,599, filed on Oct. 6, 2006, now abandoned.

(51) Int. Cl.
*A61M 31/00* (2006.01)
*A61M 1/00* (2006.01)

(52) U.S. Cl. ............ 604/67; 604/65; 604/500; 604/501; 604/153

(58) Field of Classification Search ............... 604/65, 604/67, 500, 501, 153
See application file for complete search history.

(56) References Cited

U.S. PATENT DOCUMENTS

2005/0245897 A1 * 11/2005 Bolduc et al. ............. 604/524
* cited by examiner

*Primary Examiner* — Nicholas Lucchesi
*Assistant Examiner* — Ian Holloway
(74) *Attorney, Agent, or Firm* — Jerry A. Schulman (57) ABSTRACT

An irrigation and aspiration tubing system for use with surgical handpieces and irrigation fluid supplies has a flexible tube with first and second lumens formed integrally along its length, with a first lumen used for transporting irrigation fluid to the handpiece and a second lumen used for aspiration of fluid and emulsified particles from a surgical site. The cross-sectional area of the first lumen is selected to provide a cross-sectional area available for fluid flow in excess of the cross-sectional area of a standard surgical irrigation tubes. The system also includes at least one adaptor to allow the tubing to be attached to known surgical handpieces. Preferably, a second adaptor is also provided allowing attachment to sources of irrigating fluid and aspiration vacuum. One said lumen is formed integral with either the interior or exterior surface of the flexible tube.

15 Claims, 8 Drawing Sheets

COEXTENSIVE TUBING SYSTEM FOR PHACOEMULSIFICATION HANDPIECES

This invention relates generally to surgical instruments and surgical techniques and, more particularly, to eye surgery and to phacoemulsification apparatus and methods for their use. This application is a continuation-in-part application of application Ser. No. 11/069,773, filed Mar. 1, 2005, which claims priority from provisional application Ser. No. 60/613,645, filed Sep. 27, 2004 and which also claims priority from provisional application Ser. No. 60/828,599, filed Oct. 6, 2006 all of which are incorporated herein by reference.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through a relatively small incision, allowing the lens to unfold when it is properly positioned within the capsular bag. Techniques and instruments have also been developed to accomplish the removal of the diseased lens through an equally small incision.

One such technique is known as phacoemulsification. A typical phacoemulsification system includes a handpiece having a tip sized to fit through a small incision. Within the tip a hollow needle is vibrated at ultrasonic frequencies in order to fragment the diseased lens into small enough particles to be aspirated from the eye. Commonly, an irrigation sleeve is mounted around the needle through which irrigating liquids are infused into the eye to flush the lens particles created by the vibrations. Often the needle is hollow and forms a pathway to aspirate the irrigating fluid and lens particles from the eye. In this way both aspiration and irrigation are performed by a single instrument requiring only a single incision.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small an incision as possible during such surgery is to minimization any leakage of liquid during and after surgery to prevent tissue collapse.

Separate flow paths are required for the infusing and aspirating functions to be carried out properly. This requires the use of separate lengths of flexible tubing extending from the handpiece to the flow system control module. Typically these tubing lengths are on the order of 200 to 250 cm. Because the aspiration and irrigation tubes both go from the handpiece to the control module they often become tangled with one another, making manipulation of the handpiece more difficult.

While this invention is principally described with reference to eye surgery and the use of instruments and techniques for phacoemulsification, instruments requiring separate fluid flow paths, such as for aspiration and irrigation, are known in other surgical arts as well. For example, some instruments used in liposuction (the shaping and removal of adipose tissue by breaking up the tissue and aspirating the tissue particles) also are designed to be used with separate fluid flow lines providing aspiration and irrigation.

Multichannel tubing is well represented in the prior art. U.S. Pat. Nos. 6,287,290, 6,527,761 and 6,709,401 teach and describe methods, systems and kits for lung volume reduction which utilize catheters having coaxial tubes or tubes with coextensive multiple channels for introduction such expedients as gas for inflating a balloon attached to the catheter, guide channels for the introduction of other catheters and as aspiration channels.

U.S. Pat. No. 6,143,373 teaches and describes a catheter system and method for injection of a liquid embolic composition and a solidification agent for the injection of a liquid and a solidifying agent to close off aneurysm. The multiple lumens are used for the injection of different liquids into the circulatory system.

U.S. Pat. No. 6,066,130 teaches and describes a system for delivering laser energy in which, in one embodiment, a liquid and a guide wire are fed through separate channels in a single catheter.

U.S. Pat. No. 6,013,048 teaches and describes an ultrasonic assisted liposuction system including an instrument used in liposuction, and the irrigation and aspiration functions of the instrument.

The need thus exists for aspiration/irrigation tubing apparatus and connectors that can be connected to existing surgical handpieces and control consoles without modifying the handpieces.

A further need exists for such apparatus which allows a surgeon to manipulate the handpiece without kinking the aspiration/irrigation tubing.

Further, a need exists for such tubing and connectors to be made available in inexpensive and disposable versions.

While the following describes a preferred embodiment or embodiments of the present invention, it is to be understood that these descriptions are made by way of example only and are not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further objects and characteristics of the present invention will become apparent upon consideration of the following drawings, in which.

DETAILED DESCRIPTION OF THE INVENTION

Figure 1:
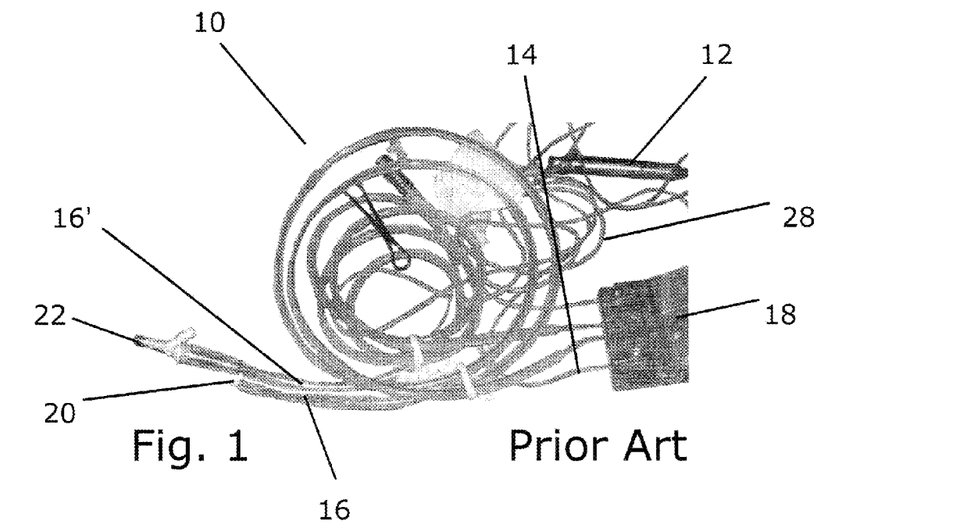
FIG. 1 illustrates a prior art surgical irrigation and aspiration apparatus and its associated tubing.

Referring now to FIG. 1, the numeral 10 indicates generally a prior art phacoemulsification apparatus consisting of a handpiece 12, a flexible, tubular aspiration line 14, flexible tubular irrigation lines 16 and 16' and a control cassette 18. Control cassette 18 provides a single control apparatus to connect a supply of irrigation solution to a phacoemulsification handpiece and to complete a path from the handpiece to an aspiration chamber for collecting the aspirated fluid, particles and the like. Electrical line 28 provides electrical power to handpiece 12.

Figure 2:
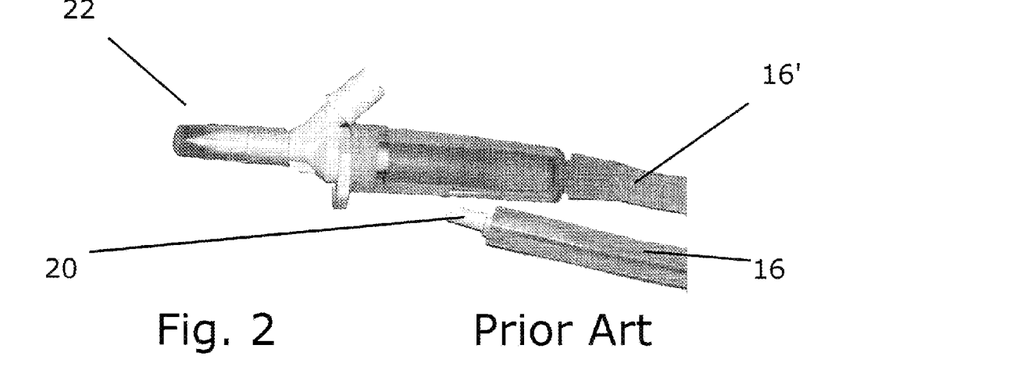
FIG. 2 is an enlarged view of both ends of the irrigation tube of FIG. 1, showing the connectors that secure the tube to the surgical handpiece and the irrigation solution supply bottle.

Referring now to FIG. 2, an enlarged view of prior art irrigation line 16 is shown. Typically, irrigation line 16 has a male end connector 20 which is inserted into an irrigation connector port on handpiece 12 in a liquid-tight friction fit. FIG. 2 also illustrates a typical irrigation fluid supply connector 22, used to connect line 16' to a container of sterile irrigating solution, such as a flexible plastic bag or the like.

Figure 3:
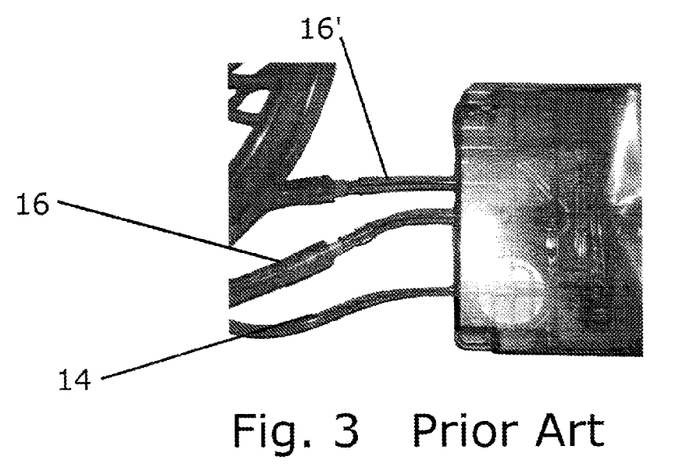
FIG. 3 is an enlarged view of the control module cassette of FIG. 1.

Referring now to FIG. 3, an enlarged view of prior art control cassette 18 is shown demonstrating the connection to cassette 18 of irrigation line 16 (to the handpiece), aspiration line 14 (from the handpiece) and irrigation line 16' (from the solution supply container).

Figures 4, 5:
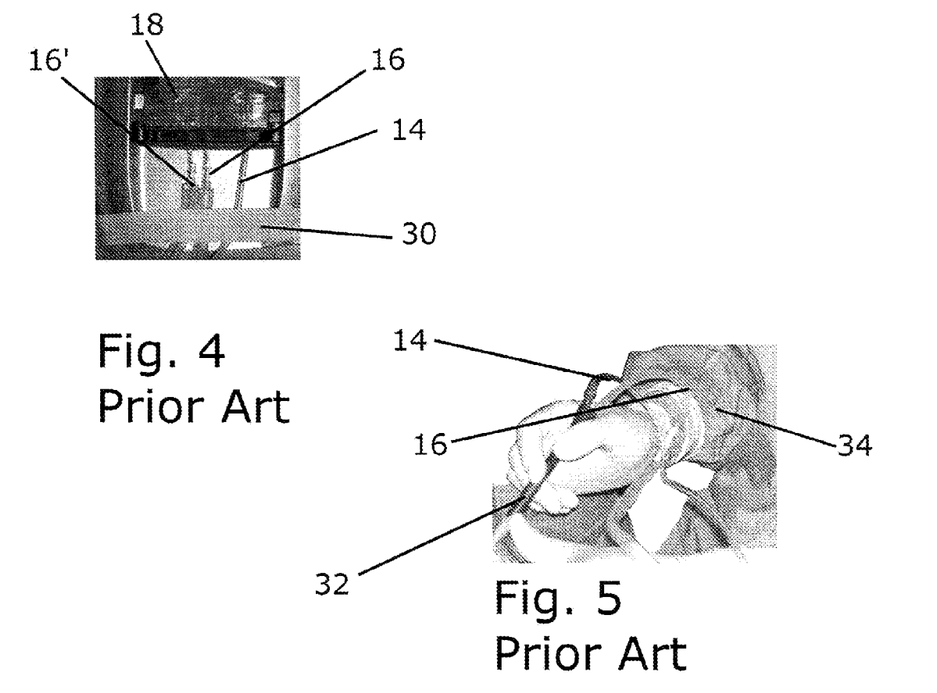
FIG. 4 is an enlarged view of the cassette of FIG. 3 showing the tubing ends taped in place.
FIG. 5 illustrates the use of a prior art handpiece with separate irrigation and aspiration tubes attached thereto.

Referring now to FIG. 4, lines 14, 16 and 16' are shown secured to prior art cassette 18 with a length of adhesive tape 30 used to secure lines 14, 16 and 16' to cassette 18 in an attempt to keep them from separating from the cassette, tangling or kinking.

Referring now to FIG. 5, a prior art handpiece 32 is shown being hand held by a surgeon 34 with aspiration line 14 and irrigation line 16 attached. Aspiration line 14 and irrigation line 16 are attached at one end to handpiece 32 and at the other end to control cassette 18. However, in between these attachment points both aspiration line 14 and irrigation line 16 are separate. During surgery, efforts must be made to prevent tubes 14, 16 from kinking and tangling. FIG. 5 shows handpiece 32 as it is held typically during surgery. As can be seen in FIG. 5, lines 14, 16 are separate and must be moved by the surgeon each time the handpiece 32 is moved. Handpiece 32 shown in FIG. 5 is typified by the model 8065 817 801 handpiece sold by Alcon.

In a first preferred embodiment of the present invention, a pair of connecting tubes are disposed one within the other to carry out the aspiration and irrigation functions without the snags and tangles experienced when separate tubes are used. As a part of the invention, adaptors are provided to connect the coaxial tubes to existing handpieces.

Figure 6:
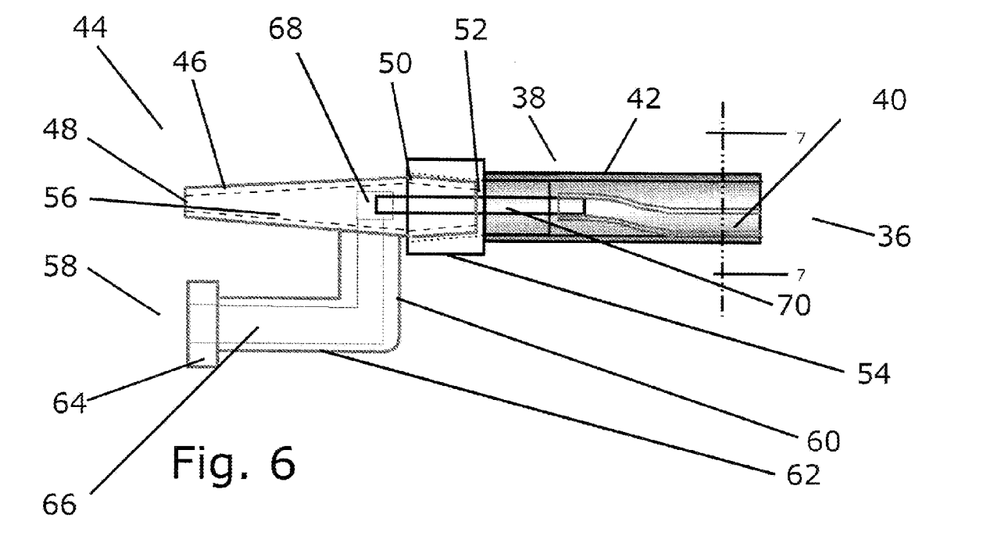
FIG. 6 is an lateral elevational view of an adaptor embodying elements of the present invention.

Referring now to FIG. 6, the numeral 36 identifies a tubing-and-adaptor apparatus constructed in accordance with the present invention. A tubing assembly 38 has an inner tube 40 disposed within an outer tube 42 with both tubes 40 and 42 manufactured from flexible material such as silicone. Tubes 40, 42 will be referred to throughout as "coaxial" even though, strictly speaking, the axes of the tubes are not required to coincide.

Figure 7:
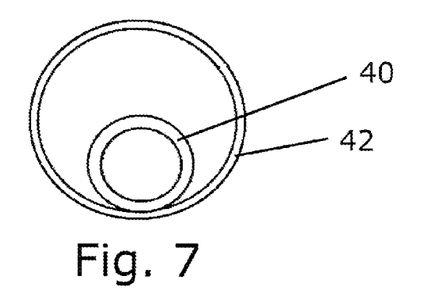
FIG. 7 is a view along line 7-7 of FIG. 6.

Referring to FIG. 7 a cross-section of tubes 40, 42 is shown, illustrating their relative dimensions. Typically a prior art irrigation tube has an inner diameter of about 3.0 mm and an outer diameter of about 5.0 mm, while a typical prior art aspiration tube has an inner diameter of about 1.0 mm and an outer diameter of about 4.0 mm.

In a preferred embodiment of the present invention, aspiration tube 40 has the same inner and outer diameters as the prior art tube and thus has a cross-sectional area of about 7.1 $mm^2$ available for fluid flow. Irrigation tube 42 has an inner diameter of about 7.0 mm and an outer diameter of about 9.0 mm, and a cross-sectional area of about 38.5 $mm^2$. When aspiration tube 40 is placed within irrigation tube 42 and the cross-sectional area measured by the inner diameter of irrigation tube 42 is subtracted from the cross-sectional area measured by the outer diameter of aspiration tube 40 there is a cross-sectional area of about 25.9 $mm^2$ available for irrigation flow, or 18.8 $mm^2$ more than with a conventional irrigation tube. This creates a flow volume 3.6 times greater than that of a prior art irrigation tube, making possible increased irrigation flow while at the same time keeping the irrigation and aspiration tubes from becoming tangled.

FIG. 6 shows tubing assembly 38 attached to an adaptor 44 constructed to allow tubing assembly 38 to be attached to a conventional phacoemulsification handpiece. Adaptor 44 has a first, generally horizontal and tapered hollow plug 46 having a first, open end 48 with plug 46 tapering outwardly from end 48 to a break 50 and, thereafter, tapering inwardly to a second open end 52. Integrally formed with adaptor 44 is a collar 54 within which second end 52 is disposed. A plug channel 56 extends through plug 46 from first end 48 to second end 52.

Integral with and depending from plug 46 is a port leg 58 comprising a first, downwardly depending leg segment 60 and a second leg segment 62 extending at substantially a right angle to segment 60 and terminating in a port collar 64. A port channel 66 begins at and extends through port collar 64, segment 62 and segment 60 terminating in a connector block 68. A connector tube 70, fluid-tightly attached to connector block 68 extends through and past collar 54.

As seen in FIG. 6, tube assembly 38 is connected to adaptor 44 in the following manner. Inner tube 40 is fluid tightly fit to connecting tube 70 while outer tube 42 is inserted into collar 54 and is frictionally and fluid tightly attached to tapered portion 52 of plug 46. In this fashion two separate fluid-tight flow paths are created. The first flow path extends from opening 48 and plug 46 through collar 54 and to outer tube 42. The second flow path begins at port collar 64 and extends through channel 66, connecting block 68 and straight connecting tube 70 to inner tube 40. When connected to a suitable handpiece, plug 48 is inserted into the port on the handpiece through which the irrigating solution is directed while port 58 forms an attachment point for a plug on the handpiece through which aspiration occurs.

Figure 8:
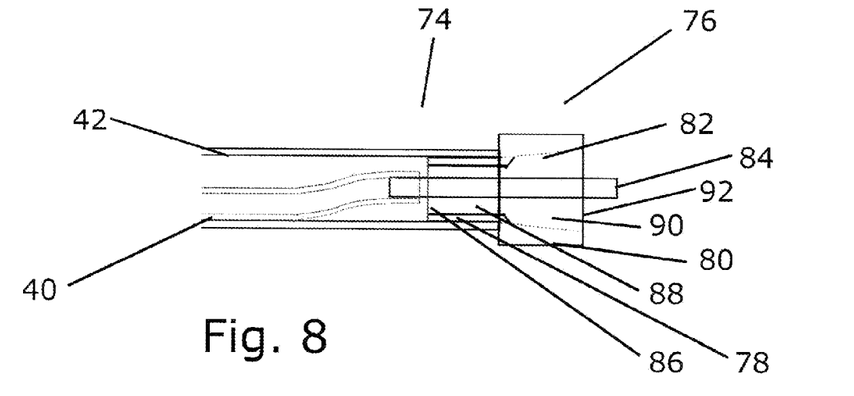
FIG. 8 is a partial sectional view of a second embodiment of an adaptor embodying the present invention.

Referring now to FIG. 8, the numeral 74 identifies a second adaptor or connector having a plug assembly 76 having a first cylindrical section 78 preferably formed as a right cylindrical section and a second or formed integrally with a second plug section 80 larger in diameter than section 78 and having a tapered inner wall 82 formed therewithin.

As seen in FIG. 8, outer tube 42 fits liquid tightly about the outer diameter of first section 78 and abuts against second section 80. Inner tube 40 is attached to a straight tube section 84 which protrudes from plug assembly 76. The configured plug assembly 76 forms a pair of flow channels, the first of which is a relatively large cylindrical flow channel 86 having a first right cylindrical cross section 88 and a second flow section with a frustoconical cross section 90, which tapers outwardly toward an opening 92 through plug section 80. The second flow path is defined by a tube 84 which is inserted, fluid tightly into inner tube 40.

Figure 9:
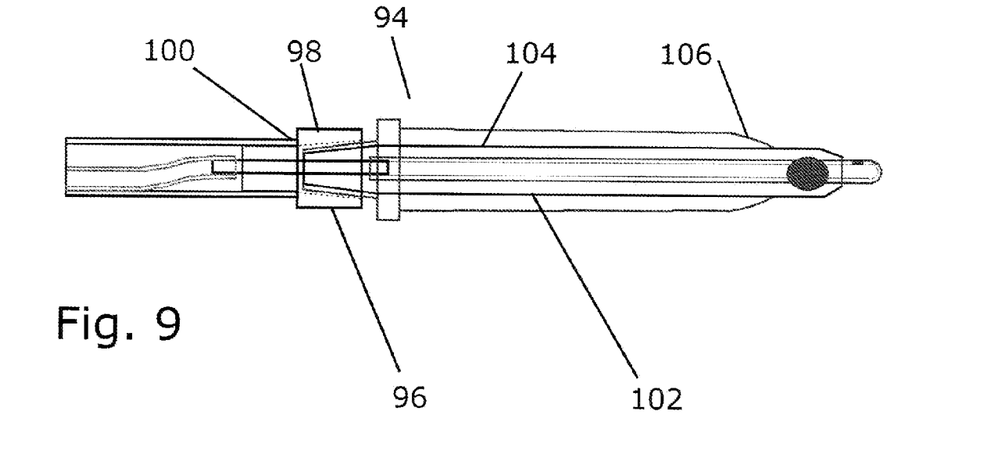
FIG. 9 is a partial sectional view of the adaptor of FIG. 8 attached to a handpiece.

Referring now to FIG. 9, the numeral 94 identifies a handpiece constructed to receive the connector and tube assembly shown in 74. Handpiece 94 has a first end 96 terminating in a hollow nipple 98 tapered outwardly from end 100 to body 102 of handpiece 94. Handpiece 94 also has a central cannula or channel 104 extending from end 96 toward tip 106. As seen in FIG. 9, adaptor and tube assembly 74 is attachable to end piece 94 by inserting the free end of straight tube 84 into cannula 104 while, at the same time, securing plug 86 to tapered end 96 in a fluid-tight fit. Thus, as seen in FIG. 9, a path for aspirating liquids is formed by tip 106, cannula 104, and inner tube 40 while a flow path from infusing liquid is formed by outer tube 42, end 96 and the channel formed through end 96.

Figure 10:
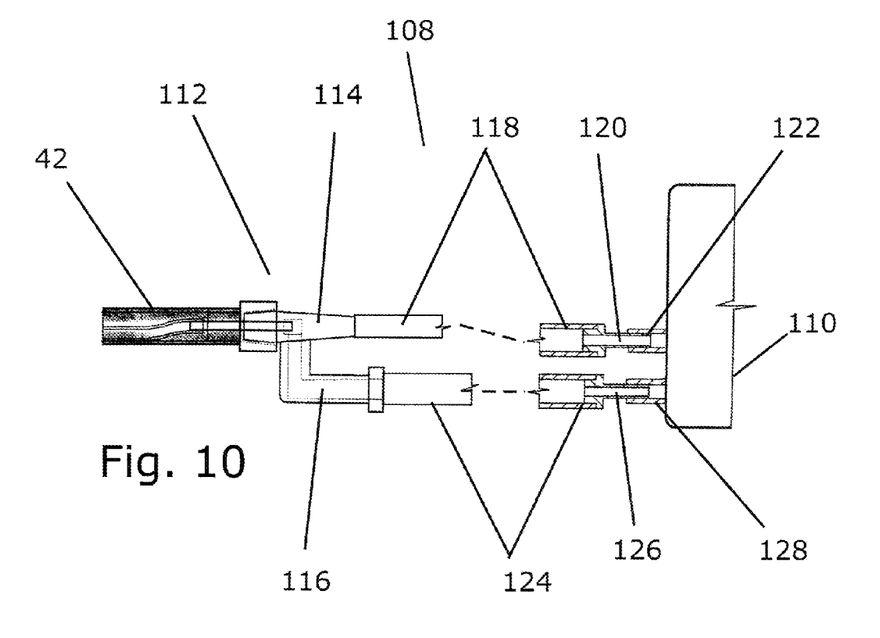
FIG. 10 is a partial sectional and elevational view showing a third embodiment of an adaptor used to connect coaxial tubing to the control cassette.

Referring now to FIG. 10, the numeral 108 illustrates a preferred method for connecting tube 42 to a control cassette 110. A cassette adaptor 112 similar in construction to adaptor 74 has an irrigation inlet port 114 and an aspiration outlet port 116. A first extension tube 118 has a plug 120 at one end sized to fit irrigation outlet port 122 on cassette 110. Tube 118 is also sized to allow a fluid-tight fit to irrigation port 114. In similar fashion, a second extension tube 124 has a plug 126 at one end sized to fit aspiration inlet port 128 on cassette 110. Tube 126 is also sized to allow a fluid-tight fit to aspiration port 116. One extension tube found to be useful in making the foregoing connections is the Nipro Extension Tube No. EX5-60AC which may be cut and the male connector ends used to make the connections to the cassette.

Figure 11:
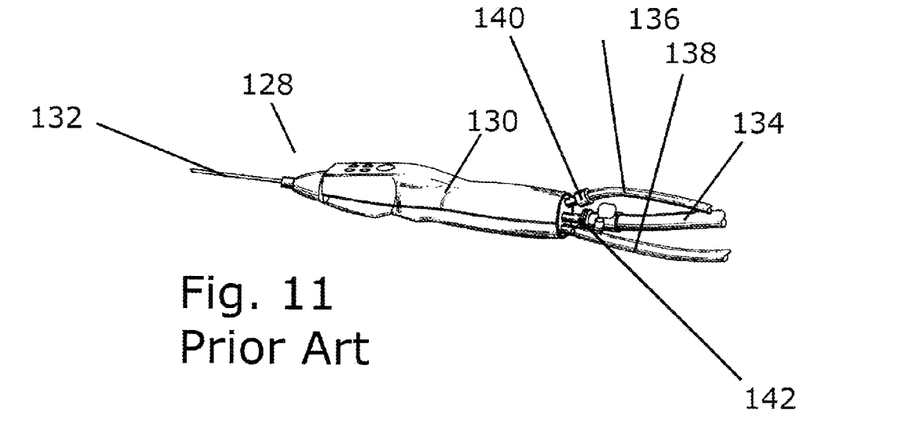
FIG. 11 illustrates a prior art liposuction instrument utilizing separate irrigation and aspiration lines.

Referring now to FIG. 11, the numeral 128 identifies a prior art surgical handpiece used in liposuction, having a body 130 and a hollow, ultrasonically-vibrating cannula 132. An aspiration line 134 draws fluid and tissue particles through hollow cannula 132, while irrigating solution is supplied via irrigation tube 136 through an irrigation channel formed in cannula 132. Electrical power is supplied to the vibrating motor in body 130 via electrical line 138.

Applying the principles of the present invention to handpiece 128, an adaptor (not shown) is designed to fit liquid-tightly at one end to aspiration port 140 and irrigation port 142 and at another end to coaxial tubes such as those shown in FIGS. 6 and 7 and as described herein.

Figure 12:
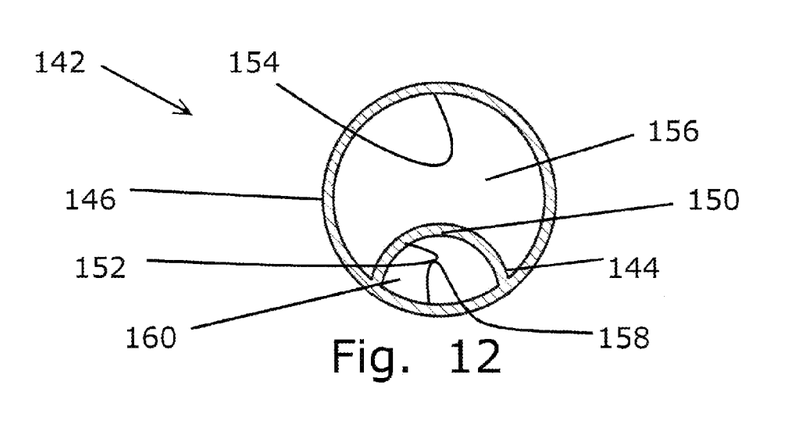
FIG. 12 is an axial cross-sectional view of a double-lumen irrigation/aspiration tube.

Referring now to FIG. 12, the numeral 142 identifies a double-lumen tube having an outer wall 144 and an inner wall 146 integral with and extending axially along an interior surface 148 of tube 142. Inner wall 146 has a first, exterior surface 150 and a second, interior surface 152. First surface 150 and a first portion 154 of interior surface 148 define a first, or irrigation lumen 156, while second surface 152 and a second portion 158 of interior surface 148 define a second, or aspiration lumen 160.

Tube 142 is preferably connected to a phacoemulsification handpiece or a control cassette such that first lumen 156 and second lumen 160 become part of two separate flow paths. A preferred method of making such a connection is to provide adaptors that will connect with tube 142 and are also configured to connect with selected handpieces, control cassettes or other flow components. One such connection system is shown in FIGS. 13 through 15.

Figure 13:
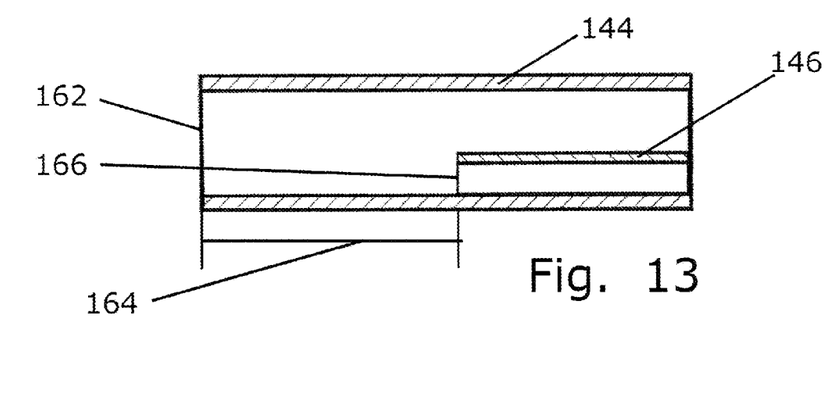
FIG. 13 is a lateral sectional view of the tube of FIG. 12.

Referring now to FIG. 13, an end of tube 142 configured to connect to an adaptor is shown in lateral cross-section. End 162 is intended to be attached to an adaptor for connection to either a phacoemulsification handpiece or a control cassette as described below. To do so, inner wall 146 is cut or foreshortened to form a setback 164 extending from end 162 to inner wall end 166.

Figure 14:
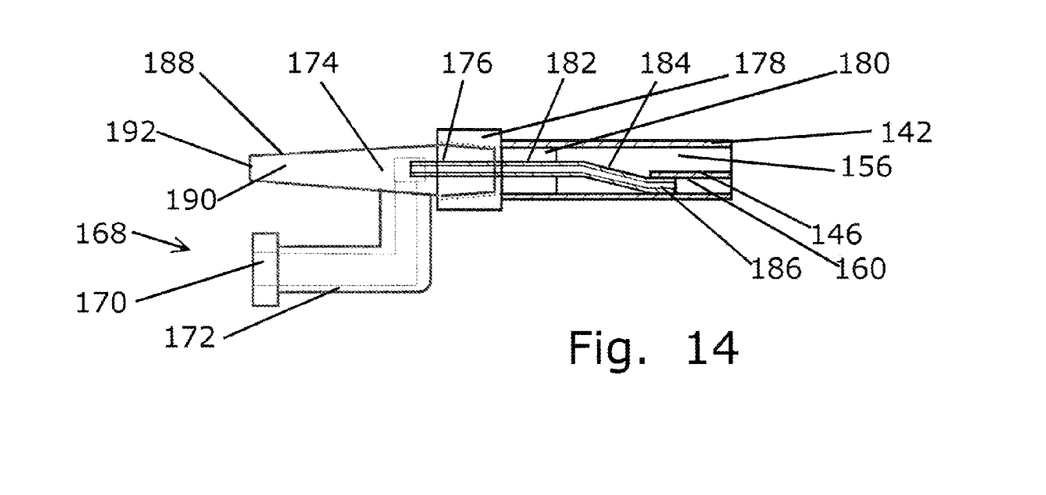
FIG. 14 is a schematic/partial sectional view of a handpiece connector adaptor for use with the tube shown in FIG. 12.
Figure 15:
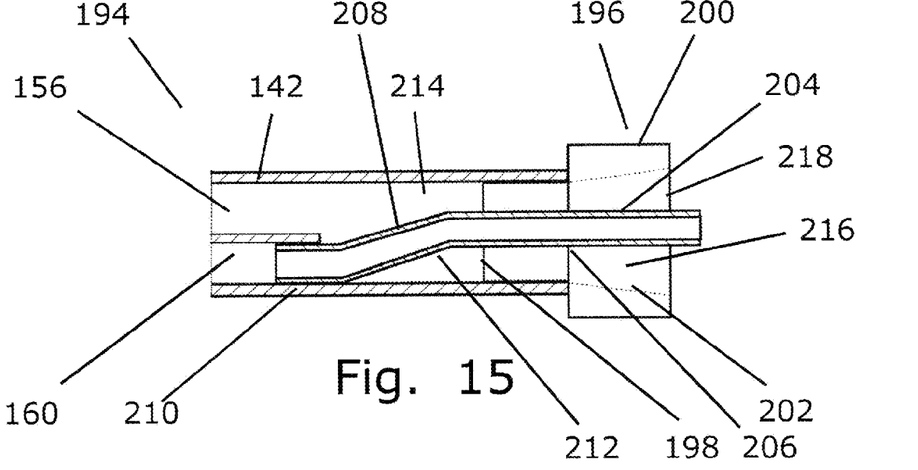
FIG. 15 is a schematic/partial sectional view of a cassette connector adaptor for use with the tube shown in FIG. 12.

Referring now to FIG. 14 a preferred handpiece adaptor 168 is shown having a port collar 170 communicating with a port channel 172 which, in turn, connects with a connection block 174 to form a flow path for aspiration of emulsified lens fragments. A collector tube 176 is fluid-tightly attached to block 174 and extends past a plug 178 into tube 142. Tube 142 is held liquid-tightly to adaptor 168 at a shoulder 180 of plug 178.

As seen in FIG. 14, collector tube 176 has a first, straight segment 182, a second, angled segment 184 and a third straight segment 186 sized and shaped to fit liquid-tightly into second lumen 160. Setback 164 is selected to allow a sufficient portion of third segment 182 to extend into second lumen 160 to form a liquid-tight fit.

First lumen 156 communicates with a hollow plug 188 having an open end 190 communicating with a plug channel 192 to form an irrigation flow path.

Referring now to FIG. 15, a preferred cassette adaptor 194 is shown having a plug assembly 196 having a first cylindrical section 198 preferably formed as a right cylindrical section and a second or formed integrally with a second plug section 200 larger in diameter than section 198 and having a tapered inner wall 202 formed therewithin.

As seen in FIG. 15, tube 142 fits liquid tightly about the outer diameter of first section 198 and abuts against second section 200. A connector tube 204 has a first, straight section 206 that extends through plug 200 and into tube 142. A second, angled section 208 is formed integrally with first section first section 206 and terminates in a third, straight section 210, which is sized and shaped to fit liquid-tightly into second lumen 160. The configured plug assembly 196 forms a pair of flow channels, the first of which is a relatively large cylindrical flow channel 212 having a first right cylindrical cross section 214 and a second flow section with a frustoconical cross section 216, which tapers outwardly toward an opening 218 through plug section 200. The second flow channel is formed by lumen 160 and tube 204.

Figure 16:
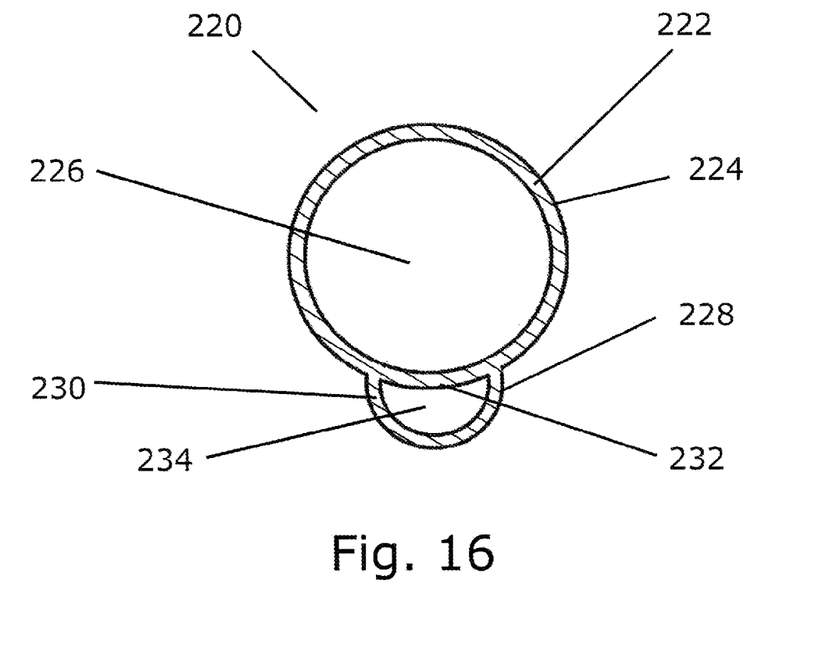
FIG. 16 is a cross-sectional view of a double-lumen tube with the second lumen formed on the exterior of the tube.

Referring now to FIG. 16 the numeral 220 identifies a double-lumen tube having a first cylindrical lumen 222 with an outer wall 224 and a first flow channel 226. A second lumen 228 is formed integrally and coextensively with first lumen 222 such that lumen 228 is not within first flow channel 226. Second lumen 228 has an outer wall 230 which, with a segment 232 of outer wall 224 forms a second flow channel 234.

Figure 17:
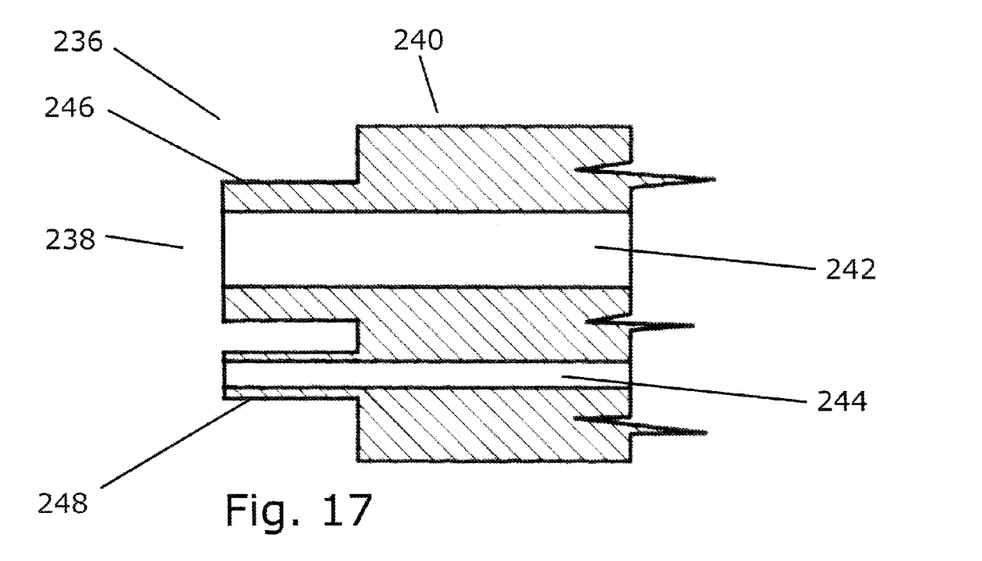
FIG. 17 is a partial sectional view of a connector adaptor for the tube of FIG. 16.

Referring now to FIG. 17, the numeral 236 identifies a sectional view of a connector adaptor to connect to tube 220. Connector 236 has an inlet end 238 formed as part of a solid body 240. A first flow passage 242 begins at end 238 and extends through body 240, and a second flow passage 244 extends through body 240.

A first nipple 246 is formed on end 238 and serves as the connector for passage 242, and a second nipple 248 is formed on end 238 and serves as the connector for passage 244.

Figure 18:
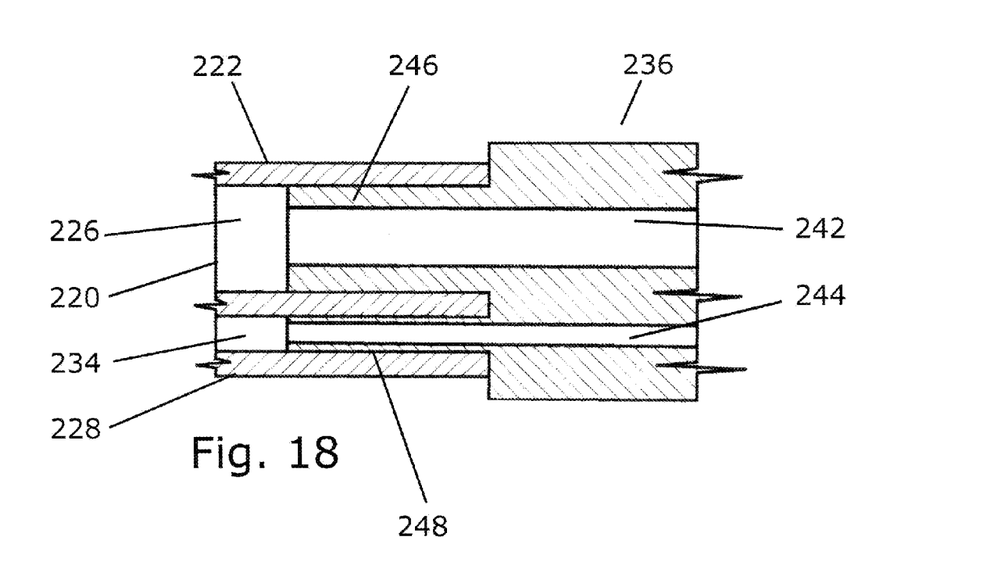
FIG. 18 is a partial sectional view showing the connection of the tube of FIG. 16 to the connector adaptor of FIG. 17.

Referring now to FIG. 18, tube 220 is shown connected to connector 236, with first lumen 222 frictionally and liquid-tightly fit to first nipple 246 and second lumen 228 frictionally and liquid-tightly fit to second nipple 248. When so connected, first flow channel 226 communicates with first flow passage 242 and second flow channel 234 communicates with second flow passage 244.

It is anticipated that a separately-configured adaptor will be supplied to fit each existing surgical handpiece and will be supplied with selected lengths of tubing constructed in accordance with the invention variations described herein. tubing.

I claim:

1. An improved fluid flow tubing system for use with a handpiece, said handpiece of the type having at least two separate fluid flow paths, said system comprising:
    means for supplying a first fluid to a first of said fluid flow paths;
    means for supplying a second fluid to a second of said fluid flow paths;
    a flexible tube having a proximal end, a distal end and an inside diameter;
    first and second separate flow lumens,
    said second lumen formed by a tube wall integral with and formed on an interior surface of said tube;
    said second lumen having an inside diameter;
    said first lumen adapted to connect to said first flow path;
    said second lumen adapted to connect to said second flow path;
    said first and second lumens disposed within said tube, said first lumen comprising the portion of the interior of said tube not occupied by said second lumen;
    means for connecting said first and second lumens to said handpiece at said tube proximal end,
    said connecting means comprising a hollow plug having first and second ends,
    said first end including a first hollow plug section with a first outside diameter,
    said first outside diameter being substantially equal to said inside diameter of said tube whereby said tube engages said first plug section in a fluid-tight fit;
    a connecting tube having first and second ends,
    said first connecting tube end having an outside diameter substantially equal to said inside diameter of said second lumen, whereby said first connecting tube end engages said second lumen in a fluid-tight fit;
    said connecting tube extending through said plug;
    means for attaching said plug to said first of said handpiece flow paths; and
    means for attaching said connecting means to said second of said handpiece flow paths.

2. The apparatus as recited in claim 1 wherein said first handpiece flow path connecting means further comprises a port channel formed at said second plug end,
    said port channel having first and second ends,
    said first port channel end being fluid-tightly attached to said first handpiece flow path,
    said second port channel end being fluid-tightly attached to said second connecting tube end.

3. The apparatus as recited in claim 1 wherein said second lumen terminates short of said tube proximal end.

4. The apparatus as recited in claim 1 wherein said second handpiece flow path connecting means further comprises a hollow plug extension fluid-tightly formed with said second plug end,
    said plug extension adapted to fluid-tightly connect to said second handpiece flow path.

5. The apparatus as recited in claim 4 wherein said first lumen has an interior cross-sectional area sufficiently large to provide a cross-sectional area for fluid flow in excess of about 7 $mm^2$.

6. The apparatus as recited in claim 3 wherein said first lumen has a cross-sectional area sufficiently large to provide a cross-sectional area for fluid flow in excess of about 7 $mm^2$.

7. The apparatus as recited in claim 4 wherein said first lumen is sufficiently large to provide a cross-sectional area for fluid flow in excess of about 7 $mm^2$.

8. An improved irrigation and aspiration tubing system for use with a phacoemulsification surgical handpiece, said handpiece of the type having a first flow path for supplying irrigating fluid from a fluid supply source to a surgical site and a second flow path connected to source of vacuum for aspirating fluid and particles from said surgical site, said system comprising:
    a flexible tube having a proximal end, a distal end and an inside diameter;
    first and second separate flow lumens, each said lumen having first and second ends,
    said first lumen adapted to connect to said irrigation flow path;
    said second lumen adapted to connect to said aspiration flow path;
    said second lumen having an inside diameter;
    said first and second lumens disposed within said tube,
    said second lumen integral with and formed on an interior surface of said tube,
    said first lumen comprising the portion of the interior of said tube not occupied by said second lumen;
    means for connecting said first lumen first end and said second lumen first end to said handpiece;
    said connecting means comprising a hollow plug having first and second ends,
    said first plug end including a first hollow plug section with a first outside diameter,
    said first outside diameter being substantially equal to said inside diameter of said tube whereby said tube engages said first plug section in a fluid-tight fit;
    a connecting tube having first and second ends,
    said first connecting tube end having an outside diameter substantially equal to said inside diameter of said second lumen, whereby said first connecting tube end engages said second lumen first end in a fluid-tight fit;
    said connecting tube extending through said plug;
    means for attaching said plug and, thereby, said first lumen first end to said handpiece irrigating fluid flow path; and
    means for attaching said second connecting tube end to said handpiece aspiration flow path.

9. The apparatus as recited in claim 8 wherein said irrigating fluid supply source and said aspiration vacuum source comprise a single flow controller, said controller having an irrigating fluid outlet and an aspiration vacuum outlet,
    said first lumen second end connecting means and said second lumen second end connecting means comprising together an adaptor,
    said adaptor configured to allow attachment of said adaptor to said irrigating fluid outlet and said aspiration vacuum outlet.

10. An improved fluid flow tubing system for use with a handpiece, said handpiece of the type having at least two separate fluid flow paths, said system comprising:
- means for supplying a first fluid to a first of said fluid flow paths;
- means for supplying a second fluid to a second of said fluid flow paths;
- a flexible tube having a proximal end, a distal end, an inside diameter, and a flow passageway;
- a flow lumen,
- said flow lumen formed by a lumen wall integral with and formed on an exterior surface of said tube;
- said flow lumen having an inside diameter;
- said tube adapted to connect to said first flow path;
- said flow lumen adapted to connect to said second flow path,
- means for connecting said tube and said flow lumen to said handpiece,
- said connecting means comprising a plug having first and second ends,
- said first end having a first hollow plug section having a first fluid passageway,
- said first plug section having a first outside diameter,
- said first outside diameter being substantially equal to said inside diameter of said tube whereby said tube engages said first plug section in a fluid-tight fit;
- said plug first end further comprising a second hollow plug section having a second fluid passageway,
- said second plug section having a second outside diameter,
- said second outside diameter being substantially equal to said inside diameter of said flow lumen whereby said flow lumen engages said second plug section in a fluid-tight fit;
- means for attaching said plug to said handpiece whereby said first fluid passageway communicates with said first fluid supply means and said second fluid passageway communicates with said second fluid supply means.

11. An improved irrigation and aspiration tubing system for use with a phacoemulsification surgical handpiece, said handpiece of the type having a first flow path for supplying irrigating fluid from a fluid supply source to a surgical site and a second flow path connected to source of vacuum for aspirating fluid and particles from said surgical site, said system comprising:
- a flexible tube having a proximal end, a distal end, an inside diameter, and a flow passageway;
- a flow lumen
- said flow lumen formed by a lumen wall integral with and formed on an exterior surface of said tube;
- said flow lumen having an inside diameter;
- said tube adapted to connect to said first flow path;
- said flow lumen adapted to connect to said second flow path;
- means for connecting said tube and said flow lumen to said handpiece,
- said connecting means comprising a plug having first and second ends,
- said first end having a first hollow plug section having a first fluid passageway,
- said first plug section having a first outside diameter,
- said first outside diameter being substantially equal to said inside diameter of said tube whereby said tube engages said first plug section in a fluid-tight fit;
- said plug first end further comprising a second hollow plug section having a second fluid passageway,
- said second plug section having a second outside diameter,
- said second outside diameter being substantially equal to said inside diameter of said flow lumen whereby said flow lumen engages said second plug section in a fluid-tight fit;
- means for attaching said plug to said handpiece whereby said first fluid passageway communicates with said first flow path and said second fluid passageway communicates with said second flow path.

12. The apparatus as recited in claim 10 wherein said irrigating fluid supply source and said aspiration vacuum source comprise a single flow controller, said controller having an irrigating fluid outlet and an aspiration vacuum outlet,
- said flow lumen second end connecting means and said second lumen second end connecting means comprising together an adaptor,
- said adaptor configured to allow attachment of said adaptor to said irrigating fluid outlet and said aspiration vacuum outlet.

13. The apparatus as recited in claim 8 wherein said first lumen has an interior cross-sectional area sufficiently large to provide a cross-sectional area for fluid flow in excess of about 7 mm$^2$.

14. The apparatus as recited in claim 10 wherein said first lumen has a cross-sectional area sufficiently large to provide a cross-sectional area for fluid flow in excess of about 7 mm$^2$.

15. The apparatus as recited in claim 11 wherein said first lumen is sufficiently large to provide a cross-sectional area for fluid flow in excess of about 7 mm$^2$.

* * * * *